(12) United States Patent
Gunkel

(10) Patent No.: US 12,109,369 B2
(45) Date of Patent: Oct. 8, 2024

(54) MEDICAL INSTRUMENT AND DEVICE HAVING ECHOGENIC MARKINGS

(71) Applicant: THÜRINGISCHES INSTITUT FÜR TEXTIL—UND KUNSTSTOFF—FORSCHUNG E.V., Rudolstadt (DE)

(72) Inventor: Holger Gunkel, Rudolstadt (DE)

(73) Assignee: Thüringisches Institute für Textile- und Kunstostoff-Forschung e.V., Rudolstadt (DE)

(*) Notice: Subject to any disclaimer, the term of this patent is extended or adjusted under 35 U.S.C. 154(b) by 709 days.

(21) Appl. No.: 15/930,619

(22) Filed: May 13, 2020

(65) Prior Publication Data
US 2020/0360660 A1    Nov. 19, 2020

(30) Foreign Application Priority Data

May 14, 2019  (DE) ...................... 10 2019 112 606.1

(51) Int. Cl.
| | | |
|---|---|---|
| *A61M 25/00* | (2006.01) | |
| *A61B 90/00* | (2016.01) | |
| *A61L 27/40* | (2006.01) | |
| *A61M 5/00*  | (2006.01) | |
| *A61M 25/01* | (2006.01) | |
| *B29C 48/00* | (2019.01) | |

(Continued)

(52) U.S. Cl.
CPC ......... *A61M 25/0045* (2013.01); *A61B 90/39* (2016.02); *A61L 27/40* (2013.01);
(Continued)

(58) Field of Classification Search
CPC .......... A61M 25/0045; A61M 25/0108; A61M 5/007; A61M 25/0009; A61M 25/0043; A61M 25/10; A61M 29/00; A61M 2025/0008; A61M 2025/1079; A61M 2205/32; A61B 90/39; A61B 2090/3925; A61B 8/12; A61B 8/4245; A61B 8/0841; A61B 8/445; A61L 27/40; A61L 2420/08;
(Continued)

(56) References Cited

U.S. PATENT DOCUMENTS

2002/0188195 A1* 12/2002 Mills .................... A61B 8/0833
600/431
2009/0162530 A1*  6/2009 Nesbitt ................. A61L 31/088
427/2.3
(Continued)

FOREIGN PATENT DOCUMENTS

DE    20 2009 001 974 U1     9/2010
DE    20 2012 013 102 U1    12/2014
(Continued)

OTHER PUBLICATIONS

European Search Report for counterpart application EP 20174058.6.

*Primary Examiner* — Phillip A Gray
(74) *Attorney, Agent, or Firm* — ProPat, LLC; Cathy Moore

(57) ABSTRACT

The present invention relates to a medical device having an improved ultrasound visibility and a very smooth surface, to methods for producing the device according to the invention and to the application of the device in therapeutic and diagnostic interventions. The improved ultrasound visibility is achieved by bubbles or closed cavities in an inner polymer layer.

23 Claims, 3 Drawing Sheets

(51) Int. Cl.
*B29C 48/09* (2019.01)
*B29C 48/21* (2019.01)
B29K 75/00 (2006.01)
B29K 509/02 (2006.01)
B29L 31/00 (2006.01)

(52) U.S. Cl.
CPC ........ *A61M 5/007* (2013.01); *A61M 25/0009* (2013.01); *A61M 25/0108* (2013.01); *B29C 48/0023* (2019.02); *B29C 48/022* (2019.02); *B29C 48/09* (2019.02); *B29C 48/21* (2019.02); A61B 2090/3925 (2016.02); A61L 2420/08 (2013.01); B29K 2075/00 (2013.01); B29K 2509/02 (2013.01); B29L 2031/7542 (2013.01)

(58) Field of Classification Search
CPC ... B29C 48/0023; B29C 48/022; B29C 48/09; B29C 48/21; B29K 2075/00; B29K 2509/02; B29L 2031/7542; A61F 2/82; A61F 2250/0096; A61F 2250/0097
See application file for complete search history.

(56) References Cited

U.S. PATENT DOCUMENTS

| | | | |
|---|---|---|---|
| 2010/0009171 A1* | 1/2010 | Greb | C08K 3/08 524/439 |
| 2011/0034609 A1* | 2/2011 | Duijnhoven Van | C08K 3/2279 524/601 |
| 2013/0158488 A1* | 6/2013 | Weaver | A61L 29/14 427/2.3 |
| 2014/0221828 A1 | 8/2014 | McKinnis et al. | |
| 2015/0023473 A1* | 1/2015 | Rodhammer | H01J 35/10 378/144 |

FOREIGN PATENT DOCUMENTS

| | | | |
|---|---|---|---|
| EP | 0552924 A1 | 7/1993 | |
| EP | 1462056 A1 | 9/2004 | |
| WO | 1998/18387 A1 | 5/1998 | |
| WO | WO-2005084956 A1 * | 9/2005 | ........... B41M 5/267 |
| WO | 2017/011522 A1 | 1/2017 | |

* cited by examiner

MEDICAL INSTRUMENT AND DEVICE HAVING ECHOGENIC MARKINGS

CROSS-REFERENCE TO RELATED APPLICATIONS

This application claims priority to German Patent Application 2019 112 606.1 filed May 14, 2019, which is hereby incorporated herein by reference in its entirety.

FIELD OF THE INVENTION

The present invention relates to a medical device having an improved ultrasound visibility, to methods for producing the device according to the invention and to the application of the device in therapeutic and diagnostic interventions.

BACKGROUND OF THE INVENTION

Ultrasound diagnostics (sonography) is globally the most commonly used imaging method in extended clinical examination. In the case of invasive procedures, it offers the possibility of harmless monitoring of the process with simultaneous possibility of intervention by the physician.

The medical devices encompass catheters, cannulas, needles, stents, implants, dilators, balloons or markers. In what follows, all these medical devices in question are called catheters by way of example. The statements made for catheters also apply to cannulas, needles, stents, implants, dilators, balloons or markers.

What is of great clinical relevance in this context is the visibility of catheters by means of ultrasound. For an optimal placement close to the desired site of action, a catheter in its entirety should be easily depictable during application up to checking of the final position.

However, because of the poor ultrasound visibility (echogenicity) of the plastics materials used, it is difficult to place and check the position of an invasive catheter. The difference in the material constants (acoustic impedance) between body tissue, on the one hand, and catheter, on the other, and the effective diameter are limiting factors in identification.

Furthermore, ultrasonic reflection is dependent on the surface shape and the orientation of the device in relation to the ultrasound beam. Cylindrical structures such as a needle, a catheter or a cannula with a smooth surface generally act like a mirror and reflect ultrasound waves in a specular manner in a fan-shaped conical pattern, which are only captured to a small extent by the receiver. Even very small deviations from the orthogonal direction relative to the incident ultrasound beam substantially reduce the intensity of the echo signal.

Catheters currently available on the market can be reliably visualized by ultrasound only at depths of a few millimetres below the skin surface. The more the orientation of the catheters approaches the direction of sound propagation, the poorer the depiction. Therefore, according to the prior art, the position of a catheter advanced into the vascular system of a patient is preferably determined with the aid of fluoroscopy. To this end, metallic markers comprised of, for example, gold, platinum, platinum-iridium or tantalum having annular or tubular structures are attached to the catheter, or the catheter material is filled as a whole or in strips with radiopaque substances such as barium sulfate. A further possibility is the specific vapor-coating or deposition of radiopaque substances at defined sites of the catheter. For this purpose, the radiopaque markers must have a certain material volume in order to keep the achievable contrast in the X-ray image at a practical level and, in all cases, must not be detachable from the catheters.

By using sonographic imaging methods for informative checking of the catheter position, it would be possible to avoid X-ray exposure.

In the case of devices comprised of metal, there is the general possibility of improving their visibility by means of subtractively generated structures in their surface such as etchings, indentations, grooves, notches, threads, projections or the like.

A multiplicity of possible solutions is based on the principle that gaseous substances have an enormous difference in acoustic impedance in relation to solids and also to human tissue. Taking advantage of the high jump in impedance at the gas/solid interface, what are proposed in many cases are substrates or coatings which have, for example, gas pockets, cavities, pores, gas-containing channels or microscopic surface structures for keeping air inclusions on the surface.

WO 9818387 discloses medical instruments, such as needles, of which part of the surface is covered with a material, such as epoxy resin, which is filled with reactive substances as bubble-generation agents. Upon contact with a liquid, which can take place upon insertion into a tissue, the substances, such as sodium hydrogencarbonate and citric acid, react to release gas and they form a multiplicity of mobile bubbles. A nonuniform ultrasound reflection occurs on such layers owing to nonuniform dimensions of the gas inclusions due to the production process. Open-pore structures bring about rough surfaces and can bring about the desired contrast only briefly, since the gas bubbles gradually dissolve and the surface is wetted with liquid.

Closed pore structures having a defined cell geometry and high homogeneity can be realized as syntactic foams through embedding of hollow spheres. DE 20 2009 001 974 discloses paint coatings containing cavities which are produced by embedding of hollow microspheres comprised of vinylidene chloride, which can on their part be filled with gas such as isobutane. Coatings generally have the disadvantage that a multiplicity of complex pretreatment and processing steps is necessary to ensure the necessary adhesion to the medical device and that there is no reliable avoidance of the coating detaching from flexible materials, especially under stress. Coatings on catheters have an influence on flexibility and the nature of the surface. Markings which are localized, discrete and produced by coating have to be produced by complex masking processes and bring about undesired elevations and roughnesses on the surface.

Rough surfaces are undesired in the case of insertable catheter designs. Unevennesses increase frictional resistance and furthermore promote attachment of microorganisms and increase the risk of catheter-associated infections. The rougher the material, the greater the number of flow changes in the micrometre range that arise, which can lead to the activation of thrombocytes.

Furthermore, catheters characterized by a multilayer structure produced by extrusion are known. By modifying individual layers, it is possible to improve the echogenic properties. EP1462056 relates to a catheter consisting of at least two layers, of which the outer layer has a greater layer thickness than the inner layer and gas bubbles are dispersed into the outer layer. The gas bubbles can be realized by expanding polymer microspheres. Layers generated in such a manner have the disadvantage that they are present on the entire length of the extruded part and thus also in regions in which they are rather undesired. The production of patterned markings for better distinguishing of endogenous structures and of method-related noises in the ultrasound image is not possible. The physical properties of the device are influenced greatly. For example, the property of transparency, which is often important for catheters, is lost.

US2014221828 discloses medical devices having chessboard-type echogenic patterns which are generated by casting or printing a metal film or by gas-filled plastics structures. The laser treatment recommended for the plastics structuring has, in the form described, the disadvantage that indentations and elevations arise on the surface owing to ablation and bubble formation. It is known that the material changes caused by laser beams take effect especially in the region close to the surface and decrease with increasing layer depth. No solution is shown as to how the effect of the laser beam can be restricted to the inside of the catheter wall and how the formation of surface unevennesses is avoided.

No technical solution has been described to date for a suitable and cost-effective production of discrete sonographic markings and labels on a catheter that have only a negligible influence on use properties.

SUMMARY OF ADVANTAGEOUS EMBODIMENTS OF THE INVENTION

Against this background, it is an object of the present invention to improve ultrasound-based image depiction in the body of a patient by creating hyperechogenic (highly reflective) areas on medical devices, especially catheters, the areas being reduced to the minimum necessary extent and, at the same time, surface smoothness not being impaired compared to conventional catheters.

To achieve the object, what is essentially provided by the invention is that discrete areas and layers of a thermoplastic plastics catheter consisting of at least two layers have a closed-pore structure which is generated by laser treatment. The desired positionally accurate realization of the cavities is achieved by the specific movement of the laser beam on the catheter surface and also by a multilayer structure with differentiated use and uniform distribution of the laser additives in the layer system.

DETAILED DESCRIPTION OF ADVANTAGEOUS EMBODIMENTS OF THE INVENTION

Figure 1A:
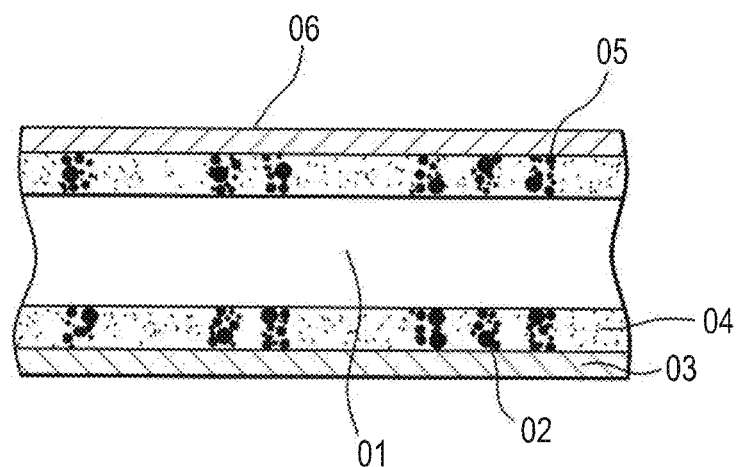
FIG. 1A is a schematic representation of a catheter produced according to the example.

The invention is thus directed to a medical device having an echogenic marking, wherein the device comprises a flexible element having a tubular shape, said element comprising an outer polymer layer and at least one inner polymer layer, and at least the outer polymer layer has a very smooth surface, characterized in that the outer polymer layer is transparent to laser radiation and an inner polymer layer contains laser additives in the form of laser absorbers, wherein the echogenic marking is formed by closed cavities or bubbles in the inner layer, which are generated by the laser additives under the action of the laser radiation.

The flexible element preferably has an outer diameter of from 6 to 18 Charrière (2 mm to 6 mm) especially of from 2.5 mm to 5 mm. The wall thickness is preferably in a range of from 0.2 mm to 0.6 mm, especially from 0.25 mm to 0.4 mm. The flexible element is useful as an ultrasound detectable catheter.

In the method of foaming by means of laser, the organic compounds contained in the plastics are broken up, destroyed and vaporized by local heating. In this process, the carbon present in the plastic oxidizes to yield $CO_2$ and forms gas bubbles. The cavities in the melt are firmly integrated in the material structure upon cooling of the material. Foaming is to be understood here to also mean the formation of a low number of bubbles at a relatively large distance from one another in the range of 5 to 200 per $mm^2$.

The use of so-called chemical blowing agents is expressly dispensed with in the context of this invention. Chemical blowing agents evolve a gas at elevated temperature as a result of thermal decomposition and can thereby form a foam structure.

Such additives are usually characterized by physiologically unfriendly ingredients or decomposition products and not suitable for medical use. Moreover, the chemical blowing agents are not activated in a location-accurate manner.

For the heat input, a laser beam is directed to the surface to be foamed. By means of a computer-controlled optical system, rapidly deflectable laser pulses having the desired power can act specifically on the sites to be foamed.

The introduction of heat is exactly defined thermally and geometrically. Both large-area regions and small-area labels, patterns and markings can be foamed with high precision.

In the interaction with laser light, plastics differ from many other materials in that they absorb the energy to a different extent, depending on the wavelength of the light.

Most plastics are laser-transmissive, i.e. they show no interaction with the laser radiation, in the region of the NIR/IR wavelengths. To utilize the advantages of the laser, easily dispersed absorbers are introduced into specific layers of the catheter and thus ensure a positionally accurate introduction of heat upon irradiation. Preferably, the laser additives are introduced into an inner layer of the catheter and are always covered by an outer layer without laser additives. This feature, together with the elastic properties of the polymer layers, means that effects on surface roughness or surface unevennesses due to foam formation are negligible. By selection of suitable absorber substances with small particle size and small use amounts, it is possible to avoid negative influences on mechanical and optical properties as far as possible.

Nanoscale mixed metal oxides in particular, such as indium or antimony tin oxide, are suitable as absorber additives for transparent materials. Nanoscale absorber additives contribute to maintenance of transparency to visible light and achievement of a uniform size and distribution of the cavities, and this has an advantageous effect on the design of patterns or letterings and on ultrasound visibility.

For the foaming of plastic, cost-effective diode-pumped solid-state lasers and fibre lasers in the wavelength range of 1064 nm are available, as are similarly also used for marking and labelling. For even more exact markings and less thermal influence on the base material, it is also possible to use technically more complex instruments with wavelengths of only 532 nm or even 355 nm.

The markings according to the invention are characterized by a closed-pore structure, the cavities of which have a virtually spherical shape in the size range from 5 to 50 µm and are only localized in the interior of the polymer layers of the catheter. By varying the additives and the laser parameters, such as power density, pulse frequency and deflection speed, it is possible to specifically set the foaming intensity. The parameters are chosen such that the desired pore size and pore number arises. Although ultrasound visibility increases with greater pore diameters, the size thereof can be limited depending on the wall thickness. It became apparent that just a pore number of 10-50 on an area of 1 mm² brings about a sufficient improvement in marking visualization in ultrasound diagnostics.

A major aspect of the present invention is that the discrete echogenic markings are produced without changes in the nature of the surface of the catheters. The claimed catheters have the advantage that the entire surface, including the marked regions, have a consistent smooth nature which is solely determined by the catheter material and the extrusion conditions.

To avoid undesired surface changes due to the laser-induced foaming and due to open pores, what is proposed is to overlay the laser-sensitive layer with an additive-free, laser-transparent cover layer which is co-extruded or produced in some other way. In the preferred technology, the differing transmission behaviour of the layers is utilized in order to specifically trigger foam formation only in an inner layer. Besides the preferred design with 2 layers, the catheter can comprise yet further polymer layers. By embedding the laser-active layer between 2 laser-transparent layers, it is, for example, possible to ensure that the surface in the catheter lumen is also not influenced by the laser treatment. The elastic properties of the thermoplastic materials usually used for catheters, such as PEBAX®, polyamide, thermoplastic polyurethane, polyethylene or soft PVC (polyvinyl chloride), ensure that the deformations in the foamed layer are not transferred up to the outer surfaces of the catheter. Since a thickness of <100 µm of the cover layer is sufficient, it can usually be thinner than the foamed layer. As required for intravascular catheters according to DIN EN ISO 10555-1, the outer surface appears free of unevennesses and foreign bodies at 2.5× magnification. Surface analyses using digital 3D microscopy show that the average roughness values $R_a$, measured in accordance with DIN EN ISO 4287:2010, of the marked and the unmarked regions deviate from one another by not more than 0.2 µm.

Owing to the increased echogenicity of the markings, the medical instrument can be visually depicted with the aid of an ultrasound examination. The gas inclusions in the marked region bring about a stronger reflection of the sound waves, with the result that they are shown distinctly more brightly compared to the surrounding substances in the ultrasound image (B mode). The detectability of the catheter is thereby distinctly improved. Owing to a patterned design of the markings, simple distinguishing of endogenous structures is possible and a displacement, bend or twist is easily identifiable. Furthermore, the possibility arises of providing regions of particular interest with a scale by means of patterns and of highlighting said regions for subsequent manipulation of the catheter.

The angle-independent high scattering characteristics on the spherical gas inclusions means that a high image contrast is generated even in the case of an unfavourable inclined position of the device in relation to the incident ultrasound.

In contrast to known solutions, the design according to the invention offers the advantage that an intensifying echogenicity is brought about especially with increasing angle of incidence.

By filling one of the polymer layers with an X-ray contrast agent, such as barium sulfate or iodine-containing contrast agent, it is also possible to combine the echogenic properties with a good X-ray visibility.

Besides the use on catheters, the claimed method can also be implemented on further medical devices used within a human body. These are especially cannulas, needles, stents, implants, dilators, balloons and markers. The necessary layers comprised of thermoplastic material can be generated by extrusion, casting, shrink-wrapping or adhesion of jackets or sleeves, or coatings with polymer solutions, melts or powders.

In what follows, the invention is elucidated on the basis of an exemplary embodiment. Further details, advantages and features of the invention are immediately apparent from the claims.

Figure 1B:
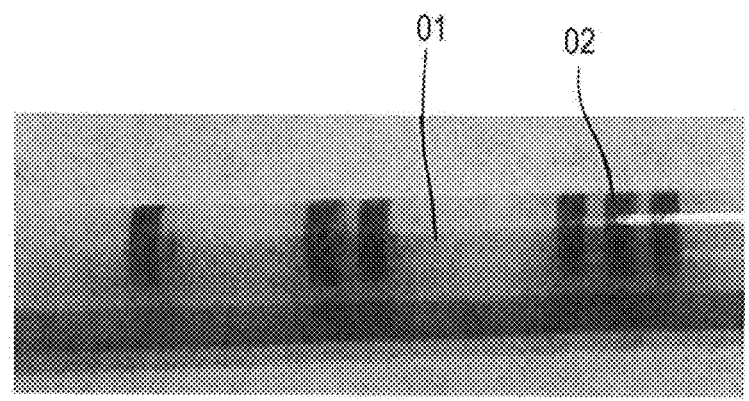
FIG. 1B is a top view photograph of a catheter produced according to the example.

As Noted Above, in the Drawings,

FIG. 1 shows a schematic representation (A) and a top view (B) of a catheter produced according to the example;

FIG. 2 shows SEM images of a cross-section (A) and of the surface (B) of a catheter produced according to the example FIG. 3 shows an ultrasound view of a catheter produced according to the example at a 0° position (A) and 45° position (B).

FIG. 1A depicts the fundamental structure of a catheter 01 provided with echogenic markings 02. The catheter has two layers, wherein the two layers 03, 04 can consist either of the same polymer matrix or of different materials and the outer layer 03 contains no additives and the inner layer 04 is filled with a laser absorber at a low fraction of 0.05 to 1% by weight. To achieve good transparency to visible light in the non-irradiated regions and a pore size and distribution in the irradiated regions that is as uniform as possible, preference is given to using laser absorbers with particle sizes <300 nm. Nanoscale laser absorber particles mean that the effectiveness of pattern generation, as measured by precision and delimitation of the contours, is optimized with minimum use of laser additive.

The gas bubbles 05 in the inner layer 04 are specifically generated by laser treatment. The laser absorbers mean that only the inner layer 04 is heated upon exposure to the laser radiation and that the formation of cavities 05 does not take effect at the surface. The outer unfilled cover layer 03 remains unchanged and can be realized with a relatively low layer thickness.

The travel path of the laser beam is programmed such that the pore structure arises in a localized manner only in the region 02 of the catheter that is to be marked. In the example depicted, the catheter contains striped markings 02 around the entire circumference. Owing to the arrangement of the stripes in groups having different numbers of stripes, an accurate assignment in the ultrasound image (FIGS. 3A and 3B) is possible.

Figure 2A:
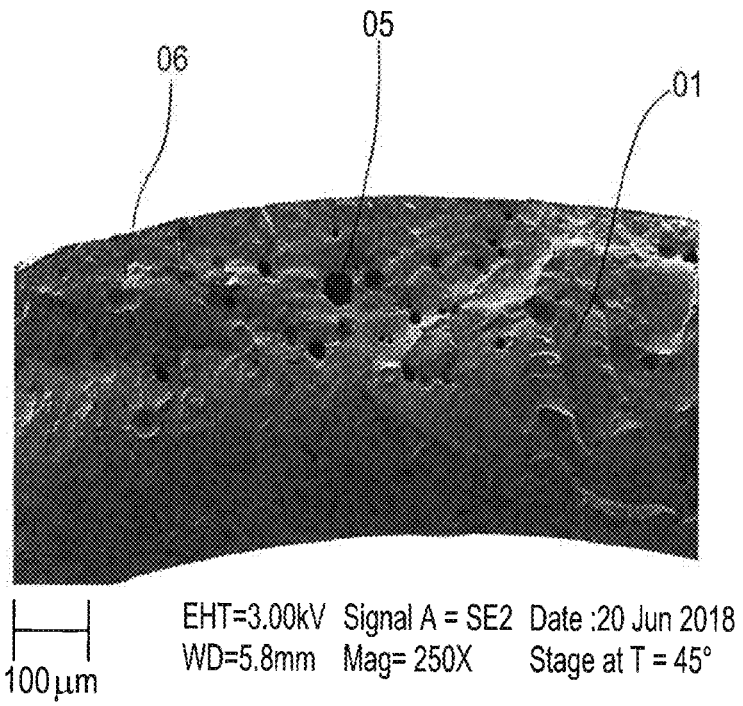
FIG. 2A is a scanning electron microscope ("SEM") image of a cross-section of a catheter produced according to the example.
Figure 2B:
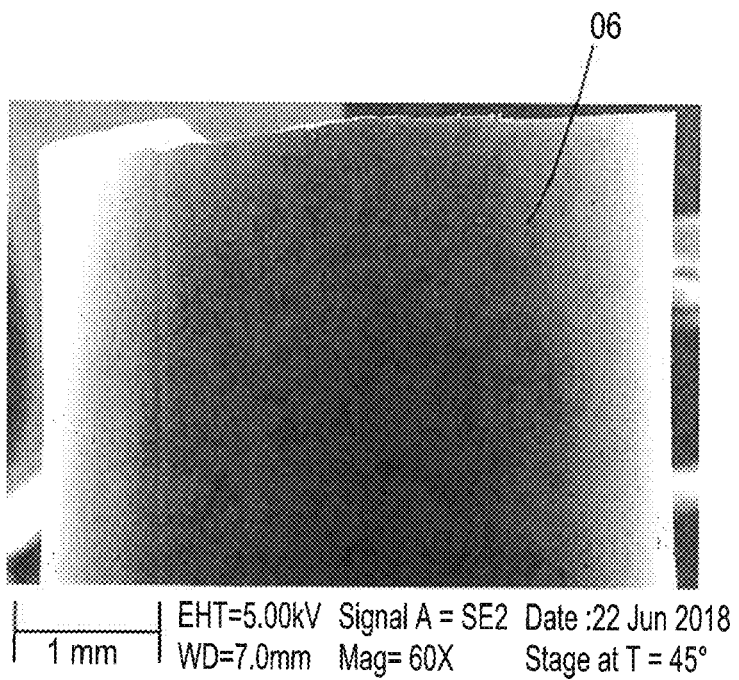
FIG. 2B is an SEM and of the surface of a catheter produced according to the example.

The SEM image of a cross-section of an additivized layer 04 of a catheter, as depicted in FIG. 2A, shows that closed-pore cavities 05 in the size range of 5 to 50 µm are formed. It is also clear that laser power decreases with increasing layer depth and that cavity size and number decrease as a result. The SEM image of the surface of a marked region of a two-layer catheter (FIG. 2B) confirms that the laser treatment does not cause any changes to the surface topography.

Ultrasound visibility was examined in a water bath at sonic angles of 0° (orthogonal angle) and 45° with a linear sonic head and a frequency of 10 MHz. To assess the contrast of the marking 10, 11 compared to unmarked regions 08, 09, the grey scale spectra of the individual image regions were compared with one another by means of a graphics program, with 100% black corresponding to a value of 0 and 100% white corresponding to a value of 255. In the ultrasound image, markings produced according to the invention stand out very well, with average brightness values of greater than 200, from the black background of the water and from the untreated regions of the catheter.

Example

This non-limiting example describes the production of an exemplary ultrasound marking according to the invention on a catheter.

A 2-layer catheter having an outer diameter of 3 mm, an outer layer thickness of 0.1 mm and an inner layer thickness of 0.3 mm was produced by means of a tube extrusion system. TPU of the type ELASTOLLAN® 1180 A10 FC was used for both layers. For the inner layer, 1% of a master batch filled with a laser additive was premixed with the TPU granular material. The master batch, which was produced on the basis of TPU by compounding with an extruder, contained 10% of antimony-doped tin oxide with particle sizes in the range of 10 to 20 nm. The tube was cut to length and labelled using a pulsed Yb fibre laser from FOBA. The rectangular markings 02 (image 1) were programmed in the dimensions 1×3 mm and realized by double lasers after 180° rotation of the tube around the entire circumference of the tube. By choosing suitable laser parameters, both grey colouring and foaming were achieved at the marked sites 02. Owing to the grey colouring, the marking can also be visually identified by the human eye. Values applied in the laser processing were a pulse width of 120 ns at a frequency of 20 kHz with a pulse energy of 4.2 watts and a wavelength of 1064 nm. Images with a scanning electron microscope of the cross-sectional area and the surface of the catheter show that cavities having a diameter of 5 to 50 μm are formed in the inner layer doped with laser additive and that the surface of the catheter remains smooth. The average number of cavities in this size range is approx. 100 per mm². The surface topography was analysed using the 3D digital microscope VHX-6000. With an arithmetic average roughness value $R_a$ (DIN EN ISO 4287:2010) of 0.19 μm, as ascertained over the entire width of the marking, and an averaged roughness depth $R_z$ of 1.7 μm, there are no relevant differences in relation to the unmarked areas (i.e. $R_a$: 0.16 μm, $R_z$: 1.6 μm) of the catheter.

Figure 3A:
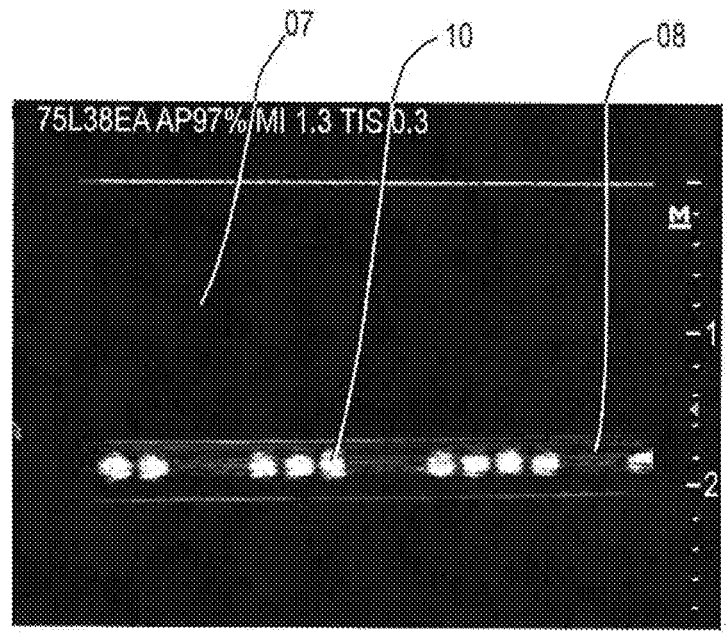
FIG. 3A is an ultrasound view of a catheter produced according to the example at a 0° position (a)
Figure 3B:
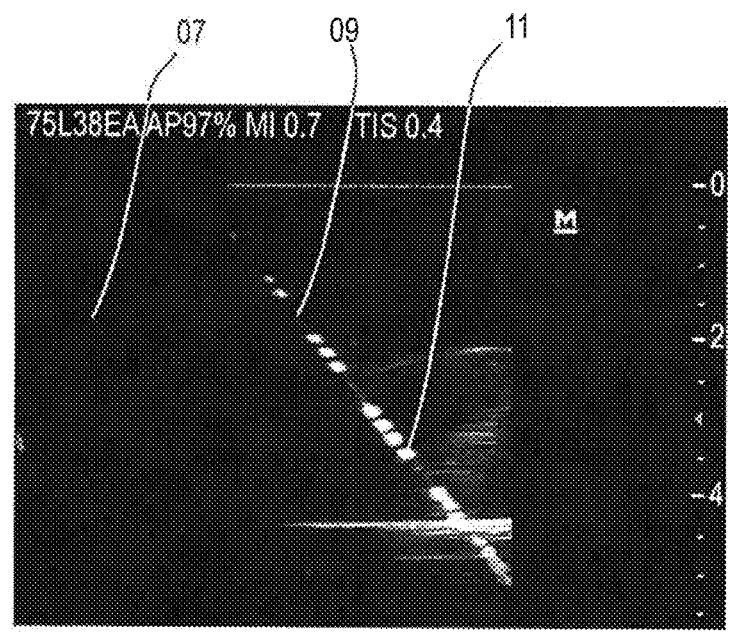
FIG. 3B is an ultrasound view of a catheter produced according to the example at a 45° position (b).

The sonographic properties were examined in a water bath and on a pork model using a DP-50 ultrasound diagnostic instrument from Mindray and a linear sonic head. FIGS. 3A and 3B show the ultrasound images of a catheter immersed in the water 07 at a 0° (3A) and 45° position (3B) in relation to the transmitted ultrasound. The following table gives an overview of the average brightness values of the various regions of the ultrasound image, as ascertained from a grey value histogram.

| Region of the image | Brightness value |
| --- | --- |
| Water 07 | 1 |
| Unmarked catheter region 0° 08 | 41 |
| Unmarked catheter region 45° 09 | 32 |
| Marking on catheter at 0° position 10 | 215 |
| Marking on catheter at 45° position 11 | 242 |

Both the subjective visual observation and the digital analysis of the images provide evidence for the high degree of functionality of the echogenic markings. An increasing visibility can be determined with increasing angle of the ultrasound in relation to the position of the catheter.

That which is claimed:

1. A medical device having an echogenic marking, the device comprising an element having a tubular shape, said element comprising an outer polymer layer and at least one inner polymer layer, and at least the outer polymer layer has a smooth surface,
   wherein the outer polymer layer is transparent to laser radiation and at least one inner polymer layer contains laser additives comprised of laser absorbers,
   the echogenic marking is comprised of closed cavities or bubbles in the at least one inner polymer layer containing laser additives, with the closed cavities or bubbles having been generated by the laser additives under an action of laser radiation,
   the laser absorbers have particle sizes in the range of <300 nm, and
   the bubbles or closed cavities have a diameter of 5 to 50 μm and a spherical or partially spherical shape.

2. The medical device having an echogenic marking according to claim 1, wherein the concentration of the laser absorbers in the at least one inner polymer layer is in the range from 0.05 to 1% by weight.

3. The medical device having an echogenic marking according to claim 1, wherein the laser absorbers are nanoscale.

4. The medical device having an echogenic marking according to claim 2, wherein the outer polymer layer has elastic properties sufficient to impart an average roughness value $R_a$ of a region of the surface of the outer polymer layer covering a region of the at least one inner polymer layer comprising the echogenic marking that deviates from a second surface roughness value $R_a$ of a second region of the surface of the outer polymer layer covering a second region of the at least one inner polymer layer not comprising the echogenic marking by not more than 0.2 μm, with said surface roughness values, $R_a$, measured in accordance with DIN EN ISO 4287:2010.

5. The medical device having an echogenic marking according to claim 1, wherein the echogenic marking is present in a form of labels, patterns or markings.

6. The medical device having an echogenic marking according to claim 1, wherein the outer polymer layer has a high transparency to visible light.

7. The medical device having an echogenic marking according to claim 1, wherein a number of bubbles or closed cavities in the marked areas is between 5 to 200 per mm².

8. The medical device having an echogenic marking according to claim 1, wherein the bubbles or closed cavities are gas-filled.

9. The medical device having an echogenic marking according to claim 1, wherein the device is a catheter, cannula, needle, stent, implant, dilator, balloon or marker.

10. The medical device having an echogenic marking according to claim 1, wherein said device further comprises an X-ray contrast agent.

11. A method for producing the medical device having an echogenic marking as claimed in claim 1 comprising
 (i) overlaying the inner layer containing laser additive with the outer layer that is transparent to laser radiation or embedding the inner layer containing laser additive between two outer layers;
 (ii) foaming areas within the inner layer containing laser additive by treating the tube with laser radiation, thereby causing the laser absorbers to generate closed cavities or vesicles within the inner layer.

12. The method as claimed in claim 11, wherein said overlaying step is selected from co-extruding, casting, shrink-wrapping, adhering or coating.

13. The method as claimed in claim 11, wherein said laser radiation has a wavelength of from 350 to 1,100 nm.

14. The method as claimed in claim 11, wherein the area is a label, pattern or marking.

15. The method as claimed in claim 11, wherein said method further comprises forming the inner layer by combining nanoscale absorber additives and polymer.

16. The method as claimed in claim 11, wherein said method further comprises filling one of the layers with an X-ray contrast agent.

17. The medical device having an echogenic marking according to claim 1, wherein marking visualization is imparted by 10 to 50 closed cavities or bubbles per 1 $mm^2$.

18. The medical device having an echogenic marking according to claim 5, wherein the pattern or marking is a line or dot.

19. The medical device having an echogenic marking according to claim 1, wherein the laser additives consist of mixed metal oxides.

20. The medical device having an echogenic marking according to claim 19, wherein the mixed metal oxide is either indium tin oxide or antimony tin oxide.

21. A medical device having an echogenic marking according to claim 1, wherein the medical device comprises particles consisting of a single mixed-metal-oxide laser absorber and the outer polymer layer and the inner polymer layer(s) are formed from the same polymer.

22. A medical device having an echogenic marking according to claim 4, wherein the outer polymer layer has a thickness of less than or equal to 100 μm.

23. A medical device having an echogenic marking according to claim 4, wherein the outer polymer layer thickness is ⅓ of the inner polymer layer thickness.

* * * * *